United States Patent [19]

Dunn et al.

[11] Patent Number: 4,525,345
[45] Date of Patent: Jun. 25, 1985

[54] CONSTANT ORDER RELEASE, SOLID DOSAGE INDOMETHACIN FORMULATION AND METHOD OF TREATING ARTHRITIS AND OTHER INFLAMMATORY CONDITIONS

[75] Inventors: James M. Dunn, Littleton; Ronald T. Haas, Highland Ranch, both of Colo.

[73] Assignee: Verex Laboratories, Inc., Englewood, Colo.

[21] Appl. No.: 637,843

[22] Filed: Aug. 6, 1984

Related U.S. Application Data

[63] Continuation of Ser. No. 334,124, Dec. 24, 1981, abandoned.

[51] Int. Cl.$^3$ .......................... A61K 9/22; A61K 9/30; A61K 9/52; A61K 9/56
[52] U.S. Cl. .......................... 424/22; 424/19; 424/35
[58] Field of Search .......................... 424/19-22, 424/35

[56] References Cited

U.S. PATENT DOCUMENTS 3,557,279  1/1971  Morse .......................... 424/20
4,308,251  12/1981  Dunn et al. .......................... 424/19
4,343,789  8/1982  Kawata et al. .......................... 424/78

FOREIGN PATENT DOCUMENTS 1146866  5/1983  Canada.
58-144316  8/1983  Japan.
58-170712  10/1983  Japan.
WO81/01652  6/1981  PCT Int'l Appl.

OTHER PUBLICATIONS

Suryakusuma et al, C.A. 102 #67344h (1985) of J. Pharm. Pharmacol. 36(8): 497-501 (1984), Encapsulated Hydrophilic Polymer Beads Containing Indomethacin as Controlled Release Drug Delivery Systems.
Cristallini et al, C.A. 102 #67338j (1985) of Appl. Biochem. Biotechnol. (1984) 10: 267-272, A Controlled-Release Anti Inflammatory Drug. Studies on Microcapsules.
Ja et al, C.A. 101 #198079c (1984) of Arch. Pharmacal Res. (1984) 7(1): 33-40, Preparation and Evaluation of Ethyl Cellulose Microcapsules of Indomethacin.
Chiyoda Yakuhin C.A. 100 #12691x (1984) of JPN 58-170, 712, 07 Oct. 1983, Sustained-Release Indomethacin Tablets.
Chiyoda Yakuhin C.A. 99 #181506q (1983) of JPN 58-144316, 27 Aug. 1983, Hydrophilic Polymers for Indomethalin Tablets.
Herzfelot et al, C.A. 99 #110606d (1983) of Pharm. ZTG, (1983) 128(29): 1589-92, Spray-Drying of Indomethacin with Polymers.
Dittgen C.A. 97 #78816T (1982) Wiss. Z. Med. Reihe (1981) 30(1): 49-51, Drug-Containing Microcarriers as Intermediates in Therapeutic Systems.
Yeh et al, C.A. 97 #203,45B (1982) of Biopharm. Drug Dispos. (1982) 3(3): 219-230, Effect of Sustained Release on the Pharmarokinetic Profile of Indomethacin in Man.
Takayama et al. C.A. 96 #223102T (1982) Chem. Pharm. Bull. (1982) 30(2): 6738 Factors Affecting the Dissolution of Indomethacin Dispersed in Various Water-Soluble Polymers.
Panoz et al, C.A. 95 #12/166d (1981) of PCT Int. Appl. 81-01,6520, 07 Dec. 1979, Galenical Preparation with Delayed Action and Programmed Release.
Dittgen et al, C.A. 89 #120878G (1978) Pharmazie 1977, 32(12) 771-7 Drug Release from Embedding Forms based on Polycacrylate.
Morse et al, C.A. 77 #52,316s (1972) of Ger. Off. 2,146,174, 30 Mar. 1972, Directly Pressed Tablets Containing Biologically Active Agents.
Morse C.A. 74 #67738T (1971) of U.S. 3 557 279, 19 Jan. 1971, Microencapsulation Form of Anti-Inflammatory Indomethacin.

*Primary Examiner*—Shep K. Rose
*Attorney, Agent, or Firm*—Niblack & Niblack

[57] ABSTRACT

A constant release rate indomethacin formulation in tablet unit dosage form, said tablet comprising an intimate admixture of from 50 to 200 mg of indomethacin, from about 1.7 to 3.7 weight percent of a slow-dissolving, water-insoluble cellulose derivative, from about 1.5 to 5.0 weight percent of a tabletting disintegrant, and from about 40 to 80 weight percent of a pharmaceutically acceptable bulking agent or diluent.

25 Claims, 1 Drawing Figure

CONSTANT ORDER RELEASE, SOLID DOSAGE INDOMETHACIN FORMULATION AND METHOD OF TREATING ARTHRITIS AND OTHER INFLAMMATORY CONDITIONS

This application is a continuation of U.S. patent application Ser. No. 334,124, filed 12/24/81, now abandoned.

BACKGROUND OF THE INVENTION

The present invention relates to an improved pharmaceutical formulation for indomethacin and more particularly relates to a solid dosage, constant order release indomethacin formulation.

The number of people who have arthritis is increasing. It is currently estimated that between 35-40 million people in the United States alone, or one in every seven individuals, have arthritic symptoms which require medical treatment. There will be one person every thirty-three seconds who will develop symptomatic arthritis and need medical treatment.

Even with the introduction of newer, non-steroidal drugs, such as indomethacin, naproxen, fenoprofen, ibuprofen and the like, aspirin remains the primary drug of choice for the treatment of the arthritic patient. However, there are some inflammatory joint diseases that are not easily managed with aspirin alone or where aspirin may not be indicated. These special situations are acute gouty arthritis, rheumetoid spondylitis and severe degenerative osteoarthritis of the hip.

When aspirin alone is ineffective, or cannot be tolerated, the non-steroidal anti-inflammatory drugs are used. The non-steroidal anti-inflammatory agents fall into three distinct chemical categories as noted in the reference pharmacology textbook, Goodman and Gilman, The Pharmacological Basis of Therapeutics, 6th Edition, Section V, Chapter 28, pages 705-713: (1) indole acetic acid derivatives which include indomethacin, a methylated indole derivative and sulindac, a fluromethinyl-sulfinyl indole derivative; (2) fenamates, a family of aspirin-like drugs that are derivatives of N-phenylanthranilic acid, including mefenamic, meclofenamic, flufenamic, tolfenamic and etofenamic acids; and (3) propionic acid derivatives. The latter group comprises the most common and widely used forms of non-steroidal phenylalkanoic acids and presently includes ibuprofen, naproxen, fenoprofen, flurbiprofen and ketoprofen.

While these compounds share common pharmacological behavior, they are distinct chemical entities, and because of their differences in chemical structure, pharmaceutical formulations that are appropriate for one or several of the above compounds, are not necessarily operable for all groups or for all members of a given group.

Indomethacin was the first commercially available, non-steroidal anti-inflammatory agent in the United States, and the product met with enormous commercial success. However, while the drug is more potent than aspirin as an anti-inflammatory agent, and has been found to possess analgesic properties as well, the severe side effects, particularly the severe gastrointestinal side effects which, on occassion have resulted in patient deaths, created a need for alternative therapy and resulted in the development and introduction of other non-steroidal anti-inflammatory agents.

However, despite its side effects, indomethacin is a very valuable therapeutic agent for conditions which do not respond to salicylate treatment, and considerable work has been done to provide improved formulations of the drug with lessened side effects. See for example U.S. Pat. Nos. 4,173,626; 4,228,160 and 4,228,161.

Much of the prior work concentrated on sustained release indomethacin preparations as methacrylic acid ester beads. See Dittgen et al Pharmazie 32(3)p.185(1977) in Chemical Abstracts 87:11555g(1977), Garcia Diss. Abstr. Int. B 38(2)pp.602-3(1977) in Chemical Abstracts 87:161724a(1977), Dittgen et al Gyogyszergszet 20(7)pp.260-262(1976) in Chemical Abstracts 87:189376h(1977); Kala et al, Pharmazie 31(11)pp. 783-9(1976) in Chemical Abstracts 86:60497c(1977) and Dittgen et al Gyogyszergszet 20(71)pp.260-2(1976) in Chemical Abstracts 85:198123p(1976).

U.S. Pat. No. 4,173,626 discloses a sustained release indomethacin capsule containing uncoated indomcthacin pellets, indomethacin pellets coated with a slow dissolving material and non-medicated pellets.

U.S. Pat. No. 4,228,161 discloses an anti-inflammatory combination having reduced ulcerogenicity comprising indomethacin and a phenylbenzoic acid compound.

U.S. Pat. No. 4,228,160 provides a complex of cyclodextrin and indomethacin which is taught to have substantially reduced ulcergenicity.

It is clear that the prior art has been concerned with reducing the ulcergenicity of indomethacin, and that while a vast body of prior art exists in the field of sustained release, buffered, enteric coated and like formulations, there has not been a simple solution to the problem posed by indomethacin.

The present invention provides an improved indomethacin formulation. Specifically, a constant release rate, solid dosage form indomethacin tablet having lessened gastrointestinal side effects, and which is simpler and less costly to produce.

SUMMARY OF THE INVENTION

The present invention provides a constant release rate indomethacin tablet which may be administered once or twice daily and which has lessened side effects over the existing, commercially available capsule dosage formulations. The constant release tablet contains a therapeutically effective amount of indomethacin admixed with a slow-dissolving, water insoluble cellulose derivative a disintegrating agent, and a bulking agent or diluent. Coloring agents or dyes as well as a tablet lubricant and the like can also be included.

DETAILED DESCRIPTION OF PREFERRED EMBODIMENTS

Figure 1:
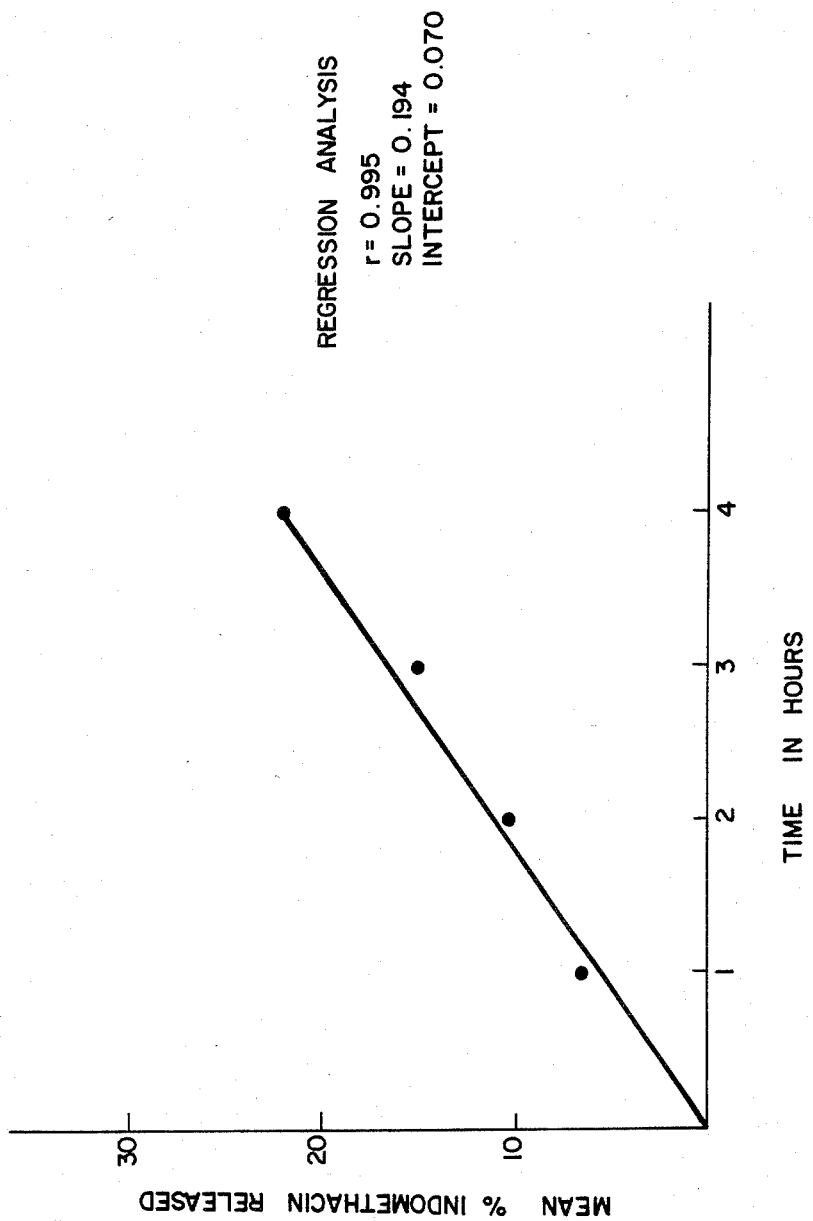
FIG. 1 is a graph showing the dissolution profile of indomethacin tablets prepared by the method of Example 1.

The constant release rate indomethacin tablet of the present invention comprises an intimate admixture of a therapeutically effective amount of indomethacin, from about 1.7 to 3.7, and preferably 2 to 3 weight percent of a slow-dissolving, water insoluble cellulose derivative, such as cellulose acetate phthalate, ethyl cellulose and the like, from about 1.5 to 5.0, preferably 1.9 to 3.2 weight percent of a disintegrant such as corn starch, methyl cellulose, hydrophobic cellulose derivatives, alginic acid or a saccharide such as lactose, maltose or fructose, and from 40-80 weight percent, preferably 55-75 weight percent of a pharmaceutically acceptable bulking agent or diluent. In addition, the tablet may include a coloring agent or dye, as well as lubricants and the like.

Preferably, each tablet contains from 50-200 mg of indomethacin and weighs from about 270 to 646 mg, respectively. Generally, for ease of administration, tablets will contain 50, 75, 100, 150 or 200 mg of indomethacin per tablet. Tablets containing 50 mg of indomethacin will weigh approximately 270 mg, tablets containing 100 mg of indomethacin will weigh approximately 538 mg and tablets containing 200 mg of indomethacin will weigh approximately 646 mg.

The preferred slow-dissolving, water insoluble cellulose derivatives are cellulose acetate phthalate and ethyl cellulose alone, or in combination with each other. Other such derivatives are well known in the art and include methyl cellulose, powdered cellulose, hydroxyethyl cellulose, hydroxypropyl cellulose, hydroxypropylmethyl cellulose, microcrystalline cellulose and the like.

Corn starch and lactose are the preferred disintegrating agents and dibasic calcium phosphate is the preferred bulking agent or diluent. Other suitable diluents include calcium phosphate, tricalcium phosphate, calcium sulfate, spray-dried lactose, anhydrous lactose, mannitol, sorbitol, microcrystalline cellulose, acacia, gelatin, sucrose, ammonium calcium alginate, alginic acid, starches, polyvinylpyrrolidone, sodium carboxy methyl cellulose and the like.

It is generally desirable to include from 0.3 to 1.5 weight percent, preferably from 0.5 to 0.9 weight percent of a lubricant in the tablet formulation of the present invention.

The term "constant release rate," as used herein, refers to a formulation wherein the in vitro release of indomethacin from the tablet, using a U.S.P. dissolution apparatus, pH 7.5, is constant and linear against time until all of the drug is released when plotted on an x,y graph using the formula $$K = dc/dt$$

wherein K=constant, dc=decreasing concentration and dt=decreasing time, a straight line is formed. Calculation of the data points by linear regression analysis should give a value of 0.85 to 1.0. A value of 1.0 is a perfect straight line.

The preparation of the indomethacin tablets of the present invention is simple, straight forward and results in a significant savings in production costs, and hence costs to the patient, over presently available capsule formulations.

Generally speaking, constant release rate indomethacin tablets are advantageously prepared by dissolving the slow-dissolving, water insoluble cellulose derivative in a suitable solvent and carefully admixing the solution with a dry blended powder of indomethacin, a disintegrating agent and a diluent to form a wet granulation. The granulation is dried, screened through a 14-20 mesh screen, and the sized granules are then compressed in a rotary or single station punch press. For ease of tabletting, it is preferred to add a lubricant such as magnesium stearate to the dried granules prior to tabletting.

The preferred solvent is a 1:1[v/v] mixture of isopropyl alcohol and methylene chloride. Other suitable solvents include, but are not limited to lower aliphatic alcohols such as methanol, n-propanol, ethanol, denatured alcohol, acetone, methyl ethyl acetate and non-chlorinated hydrocarbons.

Since indomethacin may undergo a yellowish color change on exposure to light, a coloring agent of the yellow series may be added to mask this slight color alteration. Alternatively, the tablets may be film-coated after compression to prevent this light induced alteration. The tablets of the present invention did not show any discoloration when placed in bright sunlight for 30 days as long as they remained in a light resistant container.

Turning to the preferred process of the present invention, the cellulose derivative, preferably cellulose acetate phthalate, is dissolved and dispersed in a solvent, preferably isopropyl alcohol-methylene chloride [1:1(v/v)], which is used to make a wet granulation. The amount of cellulose derivative may range from 1.7-3.7 weight percent of the final tablet weight, and preferably from 2-3 weight percent. Generally from about 15 to 25 weight percent of solvent, based on the total weight of the formulation, and preferably from about 16 to 22 weight percent is employed.

The cellulose derivative and solvent are blended until the cellulose derivative is completely dispersed and clarity of solution has been obtained. Generally, it takes between 35-40 minutes per 125 liters of fluid, using a lightening blender, to effect solution.

The granulating fluid is then added to dry blended U.S.P. indomethacin, 16-200 mesh and preferably 40-80 mesh, a bulking agent and a disintegrant, in a slow, steady stream, preferably at a rate no faster than 3 minutes per liter of solution. If the fluid is added too rapidly, it is difficult to obtain an even granulation.

Following the addition of the cellulose solution, blending is continued for from about 3 to 12 minutes, preferably 3.5 to 6 minutes per kilogram of material.

It is critical that the wet granulation be completely dried before screening. Failure to observe this technique may result in rupture of the granules and a loss of the constant release rate profile. In conventional prior art tabletting procedures, the wet granulations are generally screened immediately after formation and then dried. However, if the prior art processes are employed, the constant release rate profile of the indomethacin tablets of the present invention may be destroyed.

It is preferable to maintain the humidity below 50% both during the granulating and tabletting processes.

Indomethacin tablets made in this manner do not exhibit the proclivity for gastro-intestinal irritation which is a notable feature of regular indomethacin. They perform in a constant release rate manner in vitro as previously noted.

Because of the unique and superior constant release rate properties, indomethacin tablets made by the described process and ingredients can be administered once or possibly twice a day to provide 24 hour suppression of pain and inflammation.

EXAMPLE 1

Indomethacin tablets weighing 538 mg and containing 100 mg of indomethacin were prepared from the following formulation and by the following process.

| Ingredient | Amount |
| --- | --- |
| Indomethacin, U.S.P., 80 mesh | 100 gm |
| Dibasic Calcium Phosphate | 400 gm |
| Corn Starch | 10 gm |
| Cellulose Acetate Phthalate | 14 gm |
| Isopropyl Alcohol | 100 ml |
| Methylene Chloride | 100 ml |
| Magnesium Stearate | 4 gm |

The indomethacin, dibasic calcium phosphate and corn starch were dry blended in a Hobart mixer. The dissolved cellulose acetate phthalate was slowly added until a wet granulation was formed. The material was discharged onto paper-lined trays and dried overnight. The granules were then screened through a number 16 screen and blended with magnesium stearate. The granulate was then compressed into tablets using a rotary press. Each tablet weighed 528 mg and contained 100 mg of indomethacin with a tablet hardness of 10 kp.

EXAMPLE 2

Indomethacin tablets containing 100 mg of indomethacin were prepared from the following formulation.

| Ingredient | Amount |
| --- | --- |
| Indomethacin, U.S.P., 80 mesh | 100 gm |
| Dibasic Calcium Phosphate | 400 gm |
| Anhydrous Lactose | 10 gm |
| Opadry Blue (non-enteric) | 10 gm |
| Cellulose Acetate Phthalate | 10 gm |
| Ethyl Cellulose | 4 gm |
| Isopropyl Alcohol | 100 ml |
| Methylene Chloride | 100 ml |
| Magnesium Stearate | 4 gm |

In this formulation the indomethacin, dibasic calcium phosphate, lactose and opadry blue were dry blended for 10 minutes in a Hobart mixer. The cellulose derivatives were then dissolved and dispersed in the solvents. The granulating fluid was then added to the dry blended powder. Blending was carried out until a wet granular mass was well formed. The granulate was then discharged onto paper-lined trays and dried overnight. Following the drying process the granules were screened through a 16 mesh screen, blended with magnesium stearate and compressed on a rotary tablet press. Each 538 mg tablet contained 100 mg of indomethacin and had a hardness of 10 kp.

EXAMPLE 3

Constant release rate indomethacin tablets were made from the following formulation.

| Ingredient | Amount |
| --- | --- |
| Indomethacin, U.S.P., 80 mesh | 100 gm |
| Dibasic Calcium Phosphate | 400 gm |
| Corn Starch | 10 gm |
| Opadry Yellow (non-enteric) | 10 gm |
| Cellulose Acetate Phthalate | 14 gm |
| Isopropyl Alcohol | 100 ml |
| Methylene Chloride | 100 ml |
| Magnesium Stearate | 3 gm |

The indomethacin, dibasic calcium phosphate, corn starch and opadry yellow were placed in a Hobart mixer and dry blended for 10 minutes. The cellulose acetate phthalate was dissolved and dispersed in the solvents. After complete dissolution the solvent was added to the powder with complete mixing until a wet granulation was formed. The granulate was discharged onto paper-lined trays and dried overnight. After complete drying the granulation was reduced by screening through a number 16 mesh screen. The material was blended with magnesium stearate and compressed into tablets on a rotary press. Each 537 mg tablet contained 100 mg of indomethacin and had a hardness of 10 kp.

EXAMPLE 5

To demonstrate that the product does not have a tendency to dissolve in the stomach the following disintegration test was done using tablets made from Example 3.

TABLE 1

% Tablets Residue After 6 Hours
Disintegration, U.S.P. Basket Apparatus, No 2 Disks
Gastric Acid pH 1.2

| Start Weight mg | 6 hours weight mg | % Residue Remaining 6 hours |
| --- | --- | --- |
| 539 mg | 490 mg | 90.91% |
| 540 mg | 492 mg | 90.11% |
| 536 mg | 488 mg | 91.04% |
| 537 mg | 493 mg | 91.64% |
| 538 mg | 487 mg | 90.52% |
| 539 mg | 490 mg | 90.91% |
| 538.2 mg | 490.0 mg | 91.02% |

TABLE 2

| | Intestinal Fluid pH 7.5 | |
| --- | --- | --- |
| Start Weight mg | 6 hours weight mg | % Residue Remaining 6 hours |
| 540 mg | 108 mg | 20.0% |
| 537 mg | 105 mg | 19.6% |
| 536 mg | 100 mg | 18.7% |
| 541 mg | 110 mg | 20.3% |
| 538 mg | 106 mg | 19.7% |
| 539 mg | 107 mg | 19.9% |
| 538.5 mg | 106 mg | 19.7% |

These studies suggest that the indomethacin tablets made by the present invention are relatively resistant to disintegration in an acid media. In a neutral pH which is found beyond the stomach in the small intestine a slow, steady erosion of the tablet system is noted.

EXAMPLE 6

While the tablets showed a steady constant erosion, to be considered a true constant release rate formulation requires testing by dissolution. Tablets made by Example 1 were placed in an approved U.S.P. dissolution apparatus and assayed for indomethacin content. Twenty tablets were randomly weighed and the average tablet weight was 537.3 mg. The amount of indomethacin per tablet was reported as 94.2 mg. Dissolution was carried out using U.S.P. apparatus II, pH 7.5 150 RPM at 37 c.

| Tablet No. | % Drug Released | | | |
| --- | --- | --- | --- | --- |
| | 1 Hour | 2 Hour | 3 Hour | 4 Hour |
| 1 | 6.13 | 11.88 | 19.37 | 30.48 |
| 2 | 5.54 | 7.91 | 11.96 | 16.63 |
| 3 | 5.50 | 9.51 | 12.95 | 18.75 |
| 4 | 7.21 | 12.07 | 20.84 | 30.43 |
| 5 | 6.00 | 10.32 | 15.14 | 19.81 |
| 6 | 6.76 | 9.32 | 11.90 | 17.22 |

-continued

| Tablet No. | % Drug Released | | | |
| --- | --- | --- | --- | --- |
| | 1 Hour | 2 Hour | 3 Hour | 4 Hour |
| mean % | 6.19% | 10.17% | 15.36% | 22.22% |

Linear regression analysis of mean % drug released shows an r value of 0.995 which is graphically demonstrated in FIG. 1.

This data demonstrates that tablets made from the present formulation have a constant release rate profile and have little disintegration or tablet disruption in gastric acid.

The present formulation provides relatively low, sustained serum blood levels of indomethacin yet effectively inhibits prostaglandin synthesis and relieves pain and inflammation without the severity of gastric side effects encountered with present formulations.

EXAMPLE 7

Indomethacin tablets weighing 646 mg and containing 200 mg of indomethacin are prepared from the following formulation by the process of Example 3.

| Ingredient | Amount |
| --- | --- |
| Indomethacin, U.S.P., 60 mesh | 200 gm |
| Dibasic Calcium Phosphate | 400 gm |
| Corn Starch | 12 gm |
| Cellulose Acetate Phthalate | 17 gm |
| Isopropyl Alcohol | 100 ml |
| Methylene Chloride | 100 ml |
| Magnesium Stearate | 5 gm |
| Opadry Yellow (non-enteric) | 12 gm |

The above detailed description is given for ease of understanding only. No unnecessary limitations should be understood therefrom, as modifications will be obvious to those skilled in the art.

We claim:

1. A constant release rate indomethacin formulation in tablet unit dosage form, said tablet comprising an intimate screened, solvent wet-granulated admixture of from 50 to 200 mg of indomethacin, from about 1.7 to 3.7 weight percent of a slow-dissolving water-insoluble cellulose derivative selected from the group consisting of cellulose acetate phthalate and ethyl cellulose, dissolved in the wet-granulation solvent, the wet granulation being completely dried before screening, from about 1.5 to 5.0 weight percent of a tabletting disintegrant, and from about 40 to 80 weight percent of a pharmaceutically acceptable bulking agent or diluent.

2. The indomethacin tablet of claim 1 wherein said water-insoluble cellulose derivative is cellulose acetate phthalate.

3. The indomethacin tablet of claim 1 wherein said water-insoluble cellulose derivative is a mixture of cellulose acetate phthalate and ethyl cellulose.

4. The indomethacin tablet of claim 1 wherein said disintegrant is corn starch.

5. The indomethacin tablet of claim 2 wherein said disintegrant is corn starch.

6. The indomethacin tablet of claim 3 wherein said disintegrant is corn starch.

7. The indomethacin tablet of claim 1 wherein said disintegrant is a saccharide selected from the group consisting of lactose, maltose and fructose.

8. The indomethacin tablet of claim 2 wherein said disintegrant is a saccharide selected from the group consisting of lactose, maltose and fructose.

9. The indomethacin tablet of claim 3 wherein said disintegrant is a saccharide selected from the group consisting of lactose, maltose and fructose.

10. The indomethacin tablet of claim 1 wherein said bulking agent is dibasic calcium phosphate.

11. The indomethacin tablet of claim 2 wherein said bulking agent is dibasic calcium phosphate.

12. The indomethacin tablet of claim 3 wherein said bulking agent is dibasic calcium phosphate.

13. The indomethacin tablet of claim 4 wherein said bulking agent is dibasic calcium phosphate.

14. The indomethacin tablet of claim 5 wherein said bulking agent is dibasic calcium phosphate.

15. The indomethacin tablet of claim 6 wherein said bulking agent is dibasic calcium phosphate.

16. A constant release rate solid oral dosage indomethacin formulation in tablet unit dosage form comprising an intimate screened, solvent wet-granulated admixture of a therapeutically effective amount of indomethacin, from about 1.7 to 3.7 weight percent of a water-insoluble cellulose derivative selected from the group consisting of cellulose acetate phthalate and ethyl cellulose, dissolved in the wet-granulation solvent, the wet granulation being completely dried before screening, from about 1.5 to 5.0 weight percent of a tabletting disintegrant selected from the group consisting of corn starch or lactose and from about 40 to 80 weight percent of dibasic calcium phosphate and from 0.3 to 1.5 weight percent of a lubricant.

17. A constant release rate indomethacin formulation of claim 16 wherein said water-insoluble cellulose derivative is present in an amount of from 2.0 to 3.0 weight percent.

18. The constant release rate indomethacin formulation of claim 16 wherein said disintegrant is present in an amount of from 1.9 to 3.2 weight percent.

19. The constant release rate indomethacin formulation of claim 16 wherein said bulking agent is present in amounts of from about 55 to 75 weight percent.

20. A constant release rate solid oral dosage indomethacin tablet composition adapted to be administered to a patient suffering from arthritis once or twice a day, said tablet comprising: an intimate admixture of from 50–200 mg per tablet of indomethacin, from 1.5 to 5.0 weight percent of a water-insoluble cellulose derivative selected from the group consisting of cellulose acetate phthalate and ethyl cellulose, dissolved in the wet-granulation solvent, the wet granulation being completely dried before screening, from 1.5 to 5.0 weight percent of a tabletting disintegrant, from 40 to 80 weight percent of a bulking agent and from 0.3 to 1.5 weight percent of a lubricant.

21. The indomethacin tablet of claim 20 wherein said water-insoluble cellulose derivative is cellulose acetate phthalate, said disintegrant is corn starch and said bulking agent is dibasic calcium phosphate.

22. The indomethacin tablet of claim 20 wherein said water-insoluble cellulose derivative is a mixture of cellulose acetate phthalate and ethyl cellulose.

23. The indomethacin tablet of claim 20 wherein said disintegrant is lactose.

24. The indomethacin tablet of claim 21 wherein said cellulose derivative is present in an amount of from 2.0 to 3.0 weight percent, said disintegrant is present in an amount of from 1.9 to 3.2 weight percent, said bulking agent is present in an amount of from 55 to 75 weight percent and said lubricant is present in an amount of from 0.5 to 0.9 weight percent.

25. A method of treating the symptoms of arthritis and other inflammatory diseases comprising the steps of administering the tablet of claim 20 to a patient suffering from arthritis or another inflammatory disease once or twice a day.

* * * * *